(12) United States Patent
Parodi

(10) Patent No.: US 6,413,235 B1
(45) Date of Patent: *Jul. 2, 2002

(54) PROTECTIVE DEVICE AGAINST EMBOLIZATION IN CAROTID ANGIOPLASTY

(75) Inventor: Juan Carlos Parodi, Buenos Aires (AR)

(73) Assignee: Arteria Medical Science, Inc., San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,263

(22) Filed: May 13, 1998

(30) Foreign Application Priority Data

Mar. 13, 1998 (AR) ..................................... P 98 01 01146

(51) Int. Cl.⁷ .............................................. A61M 29/00
(52) U.S. Cl. .................... 604/104; 604/104; 604/96.01; 604/103.07; 604/103.09; 606/200
(58) Field of Search ................................. 604/104, 170, 604/96, 98, 99, 102, 96.01, 103.07, 103.09; 606/108, 198, 192, 194, 200, 127, 159, 213

(56) References Cited

U.S. PATENT DOCUMENTS

| | | | |
|---|---|---|---|
| 4,451,256 A | | 5/1984 | Weikl |
| 4,921,478 A | | 5/1990 | Solano et al. ................. 604/53 |
| 5,011,488 A | | 4/1991 | Ginsburg ..................... 606/159 |
| 5,030,227 A | * | 7/1991 | Rosenbluth et al. ......... 606/192 |
| 5,037,427 A | * | 8/1991 | Harada et al. ............... 606/108 |
| 5,071,407 A | * | 12/1991 | Termin et al. ............... 604/104 |
| 5,102,415 A | | 4/1992 | Guenther et al. ........... 606/159 |
| 5,195,980 A | * | 3/1993 | Catlin ......................... 604/167 |
| 5,221,261 A | * | 6/1993 | Termin et al. ............... 604/104 |
| 5,358,472 A | | 10/1994 | Vance |
| 5,439,446 A | * | 8/1995 | Barry .......................... 604/104 |
| 5,522,882 A | * | 6/1996 | Gaterud et al. ................. 623/1 |
| 5,549,555 A | | 8/1996 | Sohn |
| 5,549,626 A | | 8/1996 | Miller et al. ................. 606/200 |
| 5,601,591 A | * | 2/1997 | Edwards et al. ............. 606/198 |
| 5,639,274 A | * | 6/1997 | Fischell et al. ............... 604/96 |
| 5,653,689 A | * | 8/1997 | Buelna et al. ................. 604/96 |
| 5,669,924 A | * | 9/1997 | Shaknovich ................. 606/108 |
| 5,669,927 A | | 9/1997 | Boebel et al. ............... 606/180 |
| 5,833,650 A | * | 11/1998 | Imran |
| 5,895,399 A | | 4/1999 | Barbut et al. ................ 606/159 |
| 5,997,557 A | | 12/1999 | Barbut et al. ................ 606/159 |

FOREIGN PATENT DOCUMENTS

EP 0 427 429 A2 10/1990 .......... A61M/25/10

OTHER PUBLICATIONS

J. Theron, A Rationale for Endovascular Therapy With Distal Balloon Occlusion during Extracranial Atherosclerotic Carotid Artery Stenosis.

Reiner Kachel, "PTA of Carotid, Vertebral & Subclavian Artery Stenosis, An Alternative to Vascular Surgery?", Int. Angiol. 1994: 13:48–51.

* cited by examiner

Primary Examiner—Brian L. Casler
Assistant Examiner—Kevin C. Sirmons
(74) Attorney, Agent, or Firm—Fish & Neave; Nicola A. Pisano

(57) ABSTRACT

A protective device against embolization is provided for use in angioplasty of the carotid artery comprising a guide catheter that forms a lumen, and a tubular member axially movable in the lumen and having a distal end expandable against the walls of the artery. The distal end includes a drainage port with non-folding edges that communicates through the tubular member with an outlet port having an hemostatic valve and an access port that enables the introduction of a guide wire and angioplasty balloon. When deployed in the carotid artery, the distal end occludes antegrade flow through the vessel and induces retrograde flow that carries emboli through the drainage port and out of the body.

14 Claims, 3 Drawing Sheets

PROTECTIVE DEVICE AGAINST EMBOLIZATION IN CAROTID ANGIOPLASTY

BACKGROUND OF THE INVENTION

This invention relates to a protective device for protecting against embolization during carotid by temporarily reversing antegrade flow of blood stream to prevent emboli from reaching the brain.

Although traditionally conventional open surgery has been used in treatments of vascular diseases, such as stenosis of carotid artery, nowadays endovascular treatments are preferred.

These treatments carried out in the lumen of the vascular duct, and have the advantage of being less aggressive than the above mentioned open surgery.

In the case of stenosis of the carotid artery, the vascular wall is affected by a pathologic narrowing that prevents blood from flowing normally. The treatment consists in an endovascular angioplasty, resorting to a balloon in order to expand the area with stenosis and, if necessary, to deliver a stent to cover said area.

The problem that this kind of treatment has is that, when the balloon is inflated or when the stent is placed, emboli can be formed which can rapidly reach the brain, with severe consequences.

In the search of minimizing such risks, research has been carried out, such as the Echodoppler system transcranial to measure the speed of blood in the middle cerebral artery, while the surgery on the carotid artery is carried out.

In normal conditions, blood flows in an antegrade direction, i.e., upstream, so that in the carotid artery it goes from the common carotid artery to the external and internal branches. During an operation, the artery is occluded and the flow decreases, depending on the degree of collateral flow and on connections with the Circle of Willis. After the occlusion has been made, a shunt is used as a temporary conduit. One end of the shunt is connected to the internal carotid artery, while the proximal end remains open. Since the common carotid artery is occluded, blood flow is reversed, thus draining emboli to the exterior of the patient's body. This kind of treatment has enormous risks, however, since blood flow reversal can cause cerebral ischemia or hypovolemia.

It therefore would be desirable to provide a device that allows blood flow to be reversed under control, thus removing emboli generated by the angioplasty.

SUMMARY OF THE INVENTION

In view of the foregoing, a protective device against embolization is provided that overcomes the drawbacks of previously known devices and methods. The device comprises a guide catheter having a lumen, and a tubular member axially movable in the lumen and having a distal end expandable against the vascular walls of the carotid artery. The distal end includes a drainage port having non-folding edges that communicates with an outlet provided with a hemostatic valve and with an access way to the above mentioned lumen.

When the distal end of the tubular member is extended beyond the distal end of the catheter, it expands against the vascular walls. Once expanded, the distal end assumes the shape of a goblet, and the external non-folding edges occlude antegrade flow of blood. When the hemostatic valve is opened, a retrograde flow occurs that carries the emboli to the exterior of the body, where the blood may be cleansed and re-perfused. In this way, emboli are prevented from being driven by the antegrade flow to the brain through the vascular duct.

As regards the materials used for the tubular member, materials with similar properties to the known self-expanding stents can be used, such as described in Great Britain patent specification 1,205,743, to Didcott, although the material should be covered with an impermeable material in order to be part of this protective device against embolization.

BRIEF DESCRIPTION OF THE DRAWINGS

In order to accomplish a clear understanding of the subject matter of this invention, it is drawn with several figures in its preferred way, such drawings intended to be illustrative and not limiting.

In the different figures, like reference numbers refer to corresponding parts.

Figures 1A, 1B:
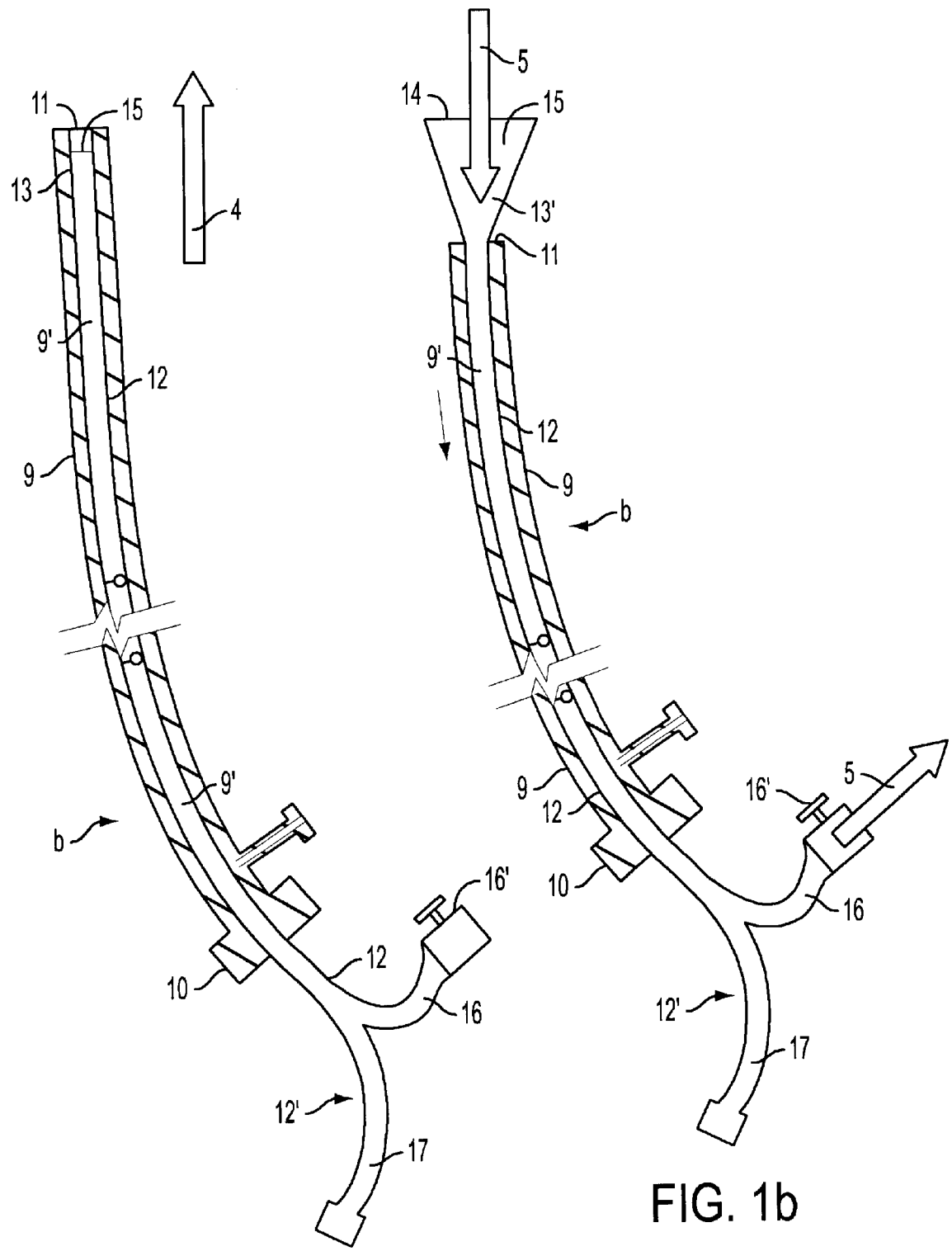
FIG. 1a is a longitudinal sectional view of the protective device with the tubular member in a retracted position.
FIG. 1b is a longitudinal sectional view like the one in FIG. 1a, in which the distal end is extended beyond the distal end of the guide catheter.
Figure 2:
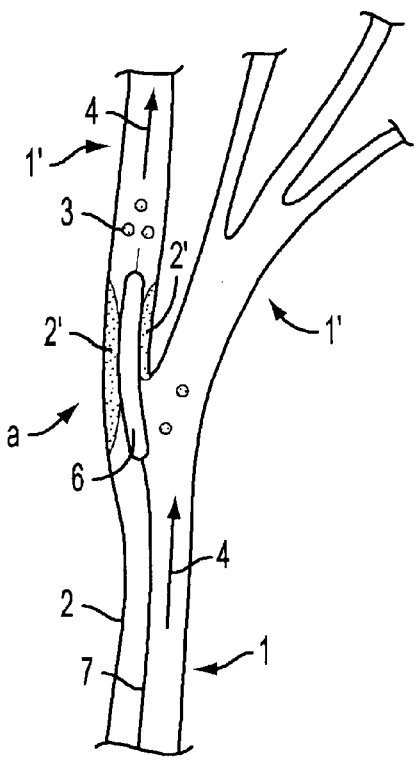
FIG. 2 is a longitudinal sectional view of the carotid artery, showing how inflation of an angioplasty balloon expands the stenosis and causes the formation of emboli, which are then carried by the antegrade flow of blood.
Figure 3:
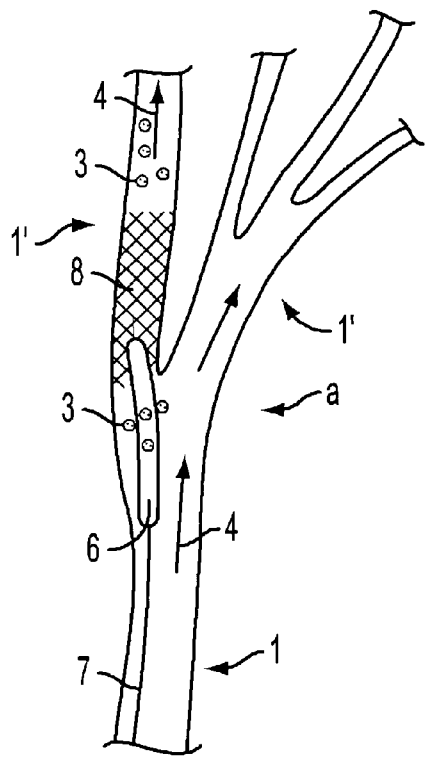
FIG. 3 is a longitudinal sectional view of the carotid artery like the one in FIG. 2, showing how the placement of a stent also generates emboli.
Figure 6:
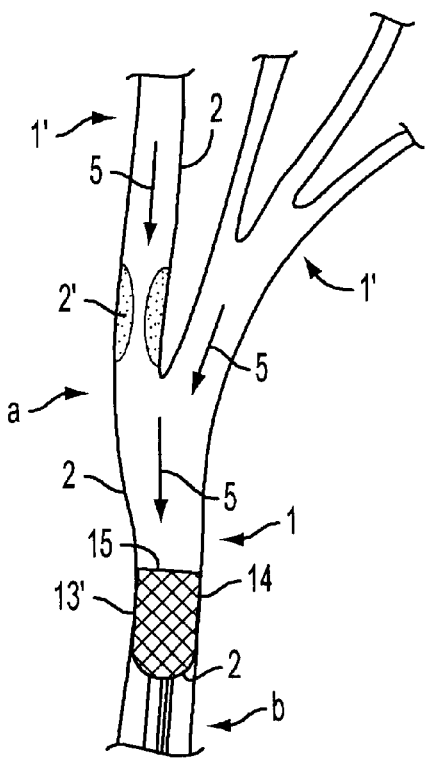
FIG. 6 is a longitudinal sectional view of the carotid artery like the one in FIG. 5, but in which the device with its distal end has expanded into the shape of a goblet when deployed.
Figure 7:
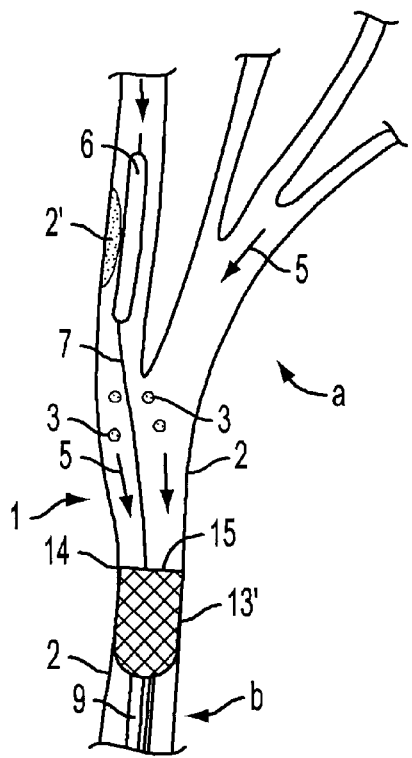
FIG. 7 is a longitudinal sectional view of the carotid artery like the one in FIG. 5, showing how retrograde flow carries emboli to the drainage port.

LIST OF REFERENCE NUMBERS (a) vascular duct (carotid artery)
(b) protective device against embolization
(1) common carotid artery
(1') external and internal branches of common carotid artery (1)
(2) vascular duct walls (a)
(2') stenosis on vascular walls (2)
(3) emboli
(4) antegrade flow of blood stream
(5) retrograde flow of blood stream
(6) angioplasty balloon
(7) guide wire
(8) stent
(9) guide catheter
(9') lumen formed by the guide catheter (9)
(10) proximal end of guide catheter (9)

(11) distal end of guide catheter (9)
(12) tubular member [axially movable inside guide catheter (9)]
(13) distal end of tubular member (12)
(13') distal end (13) expanded
(14) occluder external edges
(15) drainage port
(16) outlet port
(16') hemostatic valve
(17) access port to lumen (9')

DETAILED DESCRIPTION OF THE INVENTION

Referring to FIGS. 1a and 1b, this protective device (b) against embolization, for use during angioplasty of the carotid artery is applicable in angioplasties that treat arterial stenosis (2') of any vascular duct, such as the carotid artery. The device of the present invention can be introduced endoluminally through a blood flow path which, having normally an antegrade flow (4), by means of drainage, a retrograde flow (5) may be induced. The device comprises:

a) a guide catheter (9) having an interior lumen (9') for surgical means, such as a guide wire (7), an angioplasty balloon (6) and a stent (8); and b) a tubular member (12) that axially moves within guide catheter (9) and has a translatable impermeable distal end (13) with non-folding edges (14), which acts as an occluder of antegrade blood flow (4) when expanded against the vascular duct (a) walls (2). When deployed, the distal end (13') of the tubular means (12) forms a drainage port (15) for retrograde blood flow (5) that communicates with outlet port (16) on the proximal end (12') of tubular member (12). Outlet port (16) is provided with an hemostatic valve (16') and an access port (17) that communicates with lumen (9').

In general terms, this invention consists of a protective device (b) against embolization, in the angioplasty of the carotid artery comprising a guide catheter (9) that forms a lumen (9'), and a tubular member (12) axially movable in the lumen and having a distal end (13) expandable against the vascular walls (2). The distal end (13) includes a drainage port (15) with non-folding edges (14) that, through the tubular member (12), communicates with an outlet port (16) having an hemostatic valve (16') and an access port (17) communicating to the lumen (9').

In particular, the protective device (b) is applicable on angioplasties for treating arterial stenosis (2'), that affects walls (2) of a vascular duct (a). In a preferred application, the vascular duct (a) is the carotid artery which is composed of the common carotid artery (1) and its derivations in the external and internal branches (1'), and includes a stenosis (2') on one of those branches (1'). Inside the vascular duct (a), blood flow is in an antegrade direction (4), i.e., from the common carotid artery (1) to the branches (1').

The protective device (b) comprises a guide catheter (9), having a cylindrical and flexible body forming a lumen (9') through which surgical means, such as a guide wire (7), an angioplasty balloon (6) and a stent (8) may be delivered to the vascular duct (2). The guide catheter (9) has a proximal access opening (10) and, on the opposite end, a distal opening (11).

Within lumen (9') of guide catheter (9), a tubular member (12) is disposed for longitudinal translation with respect to the guide catheter (9). The tubular member (12) includes proximal end (12') including hemostatic valve (16') and an access port (17) and, on the distal end, a drainage port (16).

Figure 4:
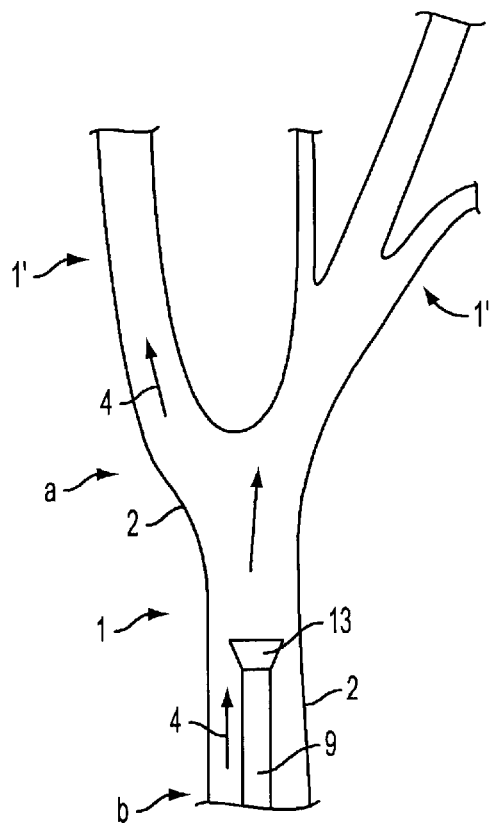
FIG. 4 is a longitudinal sectional view of the carotid artery like the one in FIG. 2, but in which the device of this invention has been placed, and the distal end has begun to be deployed.

The distal end (13) of the tubular member (12) is retracted inside the guide catheter (9) during transluminal insertion of the device, as shown in FIG. 4. The tubular member (12) moves axially between a retracted positions, wherein the distal end (13) is constrained within guide catheter (9), and an extended position, wherein the distal end (13) extends beyond the distal end of guide catheter (9). The distal end (13) is fluid impermeable and expandable and ends in external non-folding ends (14) that lie flush against the walls of the vascular duct so that emboli do not accumulate thereagainst. The non-folding edges (14) define the drainage port (15), disposed adjacent to such edges (14).

The distal end (13) is expandable against the walls (2) of the vascular duct (a) so that its external, non-folding edges (14) occlude antegrade blood flow (4) when deployed, while drainage port (16) induces retrograde flow (5) of blood through the lumen (9') to the hemostatic valve (16'). Access port (17) enables passage of a guide wire (7), an angioplasty balloon (6) or a stent (8) through tubular member (12).

Figure 5:
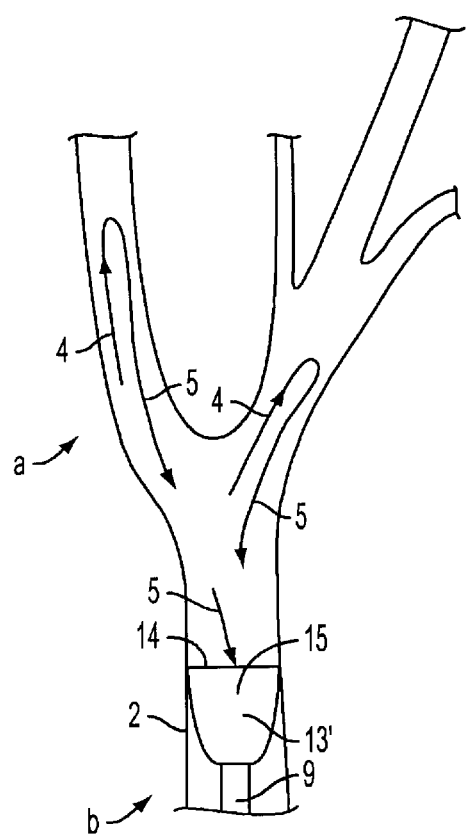
FIG. 5 is a longitudinal sectional view of the carotid artery like the one in FIG. 4, in which the distal end is shown expanded against the vascular walls to occlude the antegrade flow of blood, and induce retrograde flow to the drainage port.

In its extended position, the distal end (13) undergoes a diametral expansion (13') so that it attains a larger diameter than that of the guide catheter (9). In one embodiment, the guide catheter (9) has a diameter of 9 french, and the tubular member has a diameter less than 9 french, with the distal end (13) reaching a diameter of 12 millimeters when deployed (see FIGS. 4 and 5). When deployed against the vascular walls (2), the distal end (13') acquires a shape similar to that of a goblet, a shape that cooperates with the external, non-folding edges (14).

Operation of the device in accordance with a method of the present invention is as follows: The guide catheter (9) is placed in the vascular duct (a) with the tubular member (12) retracted within lumen (9'), i.e., with the distal end (13) constrained within the distal end of the guide catheter (9).

Axial movement of the tubular member (12) with respect to the guide catheter (9) allows the distal end (13) to extend beyond the distal end of the guide catheter (9) (see FIGS. 4 and 5), thus permitting distal end (13) to expand (13') against the vascular walls (2). Once the expansion is complete, in the shape of a goblet, the external non-folding edges (14) occlude antegrade flow (4) of blood. Guide wire (7) and angioplasty balloon (6) are then advanced to the area of the vascular walls (2) affected by stenosis (2') through access port (17), after which a stent (8) can be placed.

Because the antegrade flow (4) is occluded by the external edges (14) of the distal end (13'), when the hemostatic valve (16') of the tubular means (12) is opened, a retrograde flow (5) occurs, that carries the emboli (3) generated by the operation out of the patient's body. This retrograde flow (5), which contains emboli (3), enters through drainage port (15), and exits through the outlet port (16) and the hemostatic valve (16') to the exterior of the patient's body, where cleansing of the blood may take place. Thus, the emboli (3) are prevented from being carried by antegrade flow (4) to the brain through the vascular duct (a).

Undoubtedly, one of ordinary skill will understand that when this invention is put into practice, changes could be introduced regarding design and shape details, without departing from that principles of the present invention.

What is claimed is:

1. A device for use during carotid angioplasty or stenting comprising:

a guide catheter having proximal and distal ends, and a lumen extending therebetween;

a tubular member slidably disposed within the lumen of the guide catheter, the tubular member having first and second proximal ports, a distal end formed from a fluid impermeable material that defines a drainage port, and a lumen extending between the first and second proximal ports and the drainage port, the tubular member having a retracted position wherein the distal end is disposed within the guide catheter and has a retracted diameter suitable for endoluminal insertion, and an extended position, wherein the distal end of the tubular member extends beyond the distal end of the guide catheter and self-expands to an expanded diameter adapted to occlude antegrade blood flow in a vessel, the distal end having a non-folding edge that lies flush against the vessel to prevent the accumulation of emboli thereagainst; and a hemostatic valve disposed on the first proximal port for controlling the flow of blood therethrough.

2. The device of claim 1, wherein the distal end of the tubular member assumes a goblet shape when the tubular member is moved to the extended position.

3. The device of claim 1, wherein the second proximal port is configured to allow interventional instruments to be advanced through the lumen of the tubular member and the drainage port into the vessel.

4. The device of claim 1, wherein the guide catheter has a diameter of 9 French.

5. The device of claim 1, wherein the distal end of the tubular member has a diameter of 12 millimeters when the tubular member is in the extended position.

6. Apparatus for removing emboli generated during an angioplasty procedure, the apparatus comprising:

a guide catheter having proximal and distal ends, and a lumen extending therebetween;

a tubular member disposed within the lumen of the guide catheter, the tubular member having proximal and distal ends, the proximal end including an access port and an outlet port with a hemostatic valve, and the distal end formed from a fluid impermeable material that defines a drainage port, the tubular member further comprising a lumen coupled to the access port, the outlet port and the drainage port, wherein the tubular member is movable between a retracted position in which the distal end is disposed within the guide catheter and has a retracted diameter suitable for endoluminal insertion, and an extended position, in which the distal end of the tubular member extends beyond the distal end of the guide catheter and self-expands to an expanded diameter adapted to occlude antegrade blood flow in a vessel, the distal end having a non-folding edge that lies flush against the vessel to prevent the accumulation of emboli thereagainst.

7. The apparatus of claim 6, wherein the distal end of the tubular member assumes a goblet shape when the tubular member is moved to the extended position.

8. The apparatus of claim 6, wherein the access port is configured to allow interventional instruments to be advanced through the lumen and the drainage port into the vessel.

9. The apparatus of claim 6, wherein the guide catheter has a diameter of 9 French.

10. The apparatus of claim 6, wherein the distal end of the tubular member has a diameter of 12 millimeters when the tubular member is in the extended position.

11. A method for removing emboli generated during an angioplasty or stenting procedure, the method comprising:

providing a device comprising a guide catheter having proximal and distal ends, and a lumen extending therebetween, and a tubular member disposed within the lumen of the guide catheter, the tubular member having an access port, an outlet port with a hemostatic valve, a self-expanding distal end formed from a fluid impermeable material that defines a drainage port, and a lumen coupled to the access port, the outlet port and the drainage port;

endoluminally inserting the guide catheter to a desired location within a vessel with the tubular member in a retracted position, wherein the distal end of the tubular member is disposed within the guide catheter and has a retracted diameter;

retracting the guide catheter relative to the tubular member to move the tubular member to an extended position, wherein the distal end of the tubular member extends beyond the distal end of the guide catheter and self-expands to occlude antegrade blood flow through the vessel, the distal end having a non-folding edge that lies flush against the vessel to prevent the accumulation of emboli thereagainst;

advancing an angioplasty device into the vessel via the access port, so that a distal end of the angioplasty device is disposed distal to the distal end of the tubular member;

generating emboli while performing angioplasty with the angioplasty device; and opening the hemostatic valve to induce retrograde blood flow through the drainage port, the retrograde flow removing emboli from the vessel.

12. The method of claim 11, wherein providing a device further comprises providing a device in which the distal end of the tubular member assumes a goblet shape when the tubular member is moved to the extended position.

13. The method of claim 11, wherein providing a device further comprises providing a device in which the guide catheter has a diameter of 9 French.

14. The method of claim 11, wherein providing a device further comprises providing a device in which the distal end of the tubular member has a diameter of 12 millimeters when the tubular member is in the extended position.

* * * * *